(12) United States Patent
Faxe

(10) Patent No.: US 6,401,915 B1
(45) Date of Patent: Jun. 11, 2002

(54) PACKAGE WITH AN APPLICATOR FOR A CONTACT LENS

(76) Inventor: Thomas Faxe, Linde Allé 33, DK-3120 Dronning Mølle (DK)

( * ) Notice: Subject to any disclaimer, the term of this patent is extended or adjusted under 35 U.S.C. 154(b) by 0 days.

(21) Appl. No.: 09/529,613

(22) PCT Filed: Oct. 13, 1998

(86) PCT No.: PCT/DK98/00447

§ 371 (c)(1),
(2), (4) Date: Apr. 14, 2000

(87) PCT Pub. No.: WO99/21519

PCT Pub. Date: May 6, 1999

(30) Foreign Application Priority Data

Oct. 14, 1997 (DK) .............................. 1178/97

(51) Int. Cl.[7] .............................. A61F 9/00; B65D 81/22
(52) U.S. Cl. .......................... 206/5.1; 206/210; 294/1.2
(58) Field of Search .............................. 206/5, 5.1, 205, 206/210; 294/1.2

(56) References Cited

U.S. PATENT DOCUMENTS

| | | | | |
|---|---|---|---|---|
| 3,344,461 A | * 10/1967 | Floor | .......................... | 206/5.1 |
| 4,167,283 A | 9/1979 | Feldman | | |
| 4,332,318 A | 6/1982 | Feldman | | |
| 4,392,569 A | * 7/1983 | Shoup | .......................... | 206/5.1 |
| 4,545,478 A | * 10/1985 | Waldman | ..................... | 206/6.1 |
| 5,071,276 A | * 12/1991 | Nielsen et al. | ............... | 206/5.1 |
| 5,143,660 A | * 9/1992 | Hamilton et al. | ............ | 206/5.1 |
| 5,407,241 A | * 4/1995 | Harrison | ..................... | 294/1.2 |
| 5,415,275 A | 5/1995 | Girimont | | |
| 5,695,049 A | 12/1997 | Bauman | | |
| 5,941,583 A | * 8/1999 | Raimondi | ..................... | 294/1.2 |

FOREIGN PATENT DOCUMENTS

DE        38 22 654 A1    1/1990

* cited by examiner

Primary Examiner—Jim Foster
(74) Attorney, Agent, or Firm—McCormick, Paulding & Huber LLP

(57) ABSTRACT

A package (1) for, together with a saline solution (14), storing a contact lens (9) has an applicator for applying the contact lens in an eye (17). The package comprises a cup (4) with a convex surface (7) and a fingerstall (3) with a concave surface (11). The cup and the fingerstall are, in the unopened condition of the package, closely joined with a strip (5) which is relatively easily torn off when the package is to be opened. When the cup is removed from the fingerstall, this functions as an applicator with the wet contact lens adhering to the concave surface of the fingerstall. By means of the package, the contact lens can be applied in an eye in a clean and sterile condition and without risk of the contact lens carrying foreign bodies and bacteria-containing dirt which might irritate and damage the eye.

8 Claims, 3 Drawing Sheets

Figure 5:
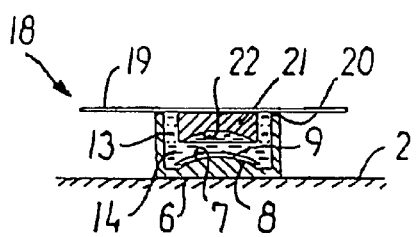

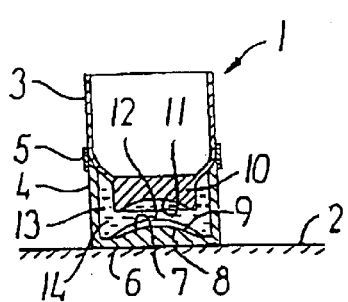
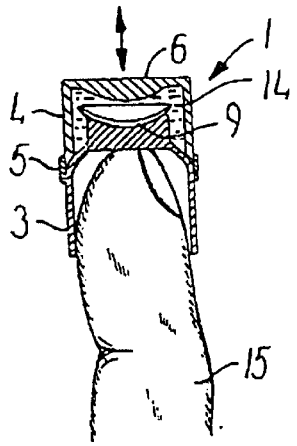
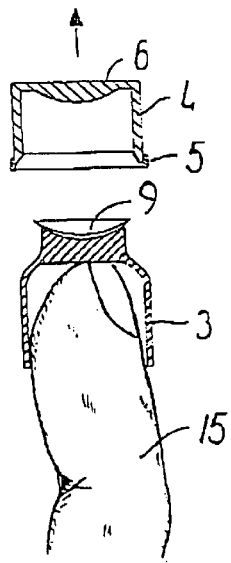
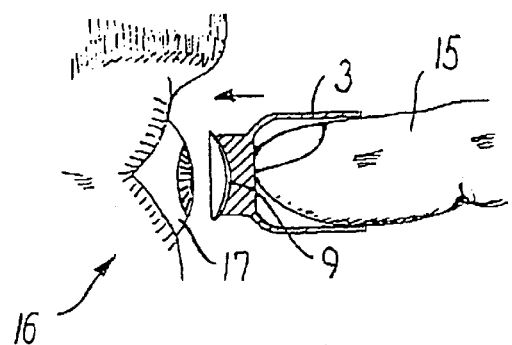
FIG. 1
FIG. 2
FIG. 3
FIG. 4

PACKAGE WITH AN APPLICATOR FOR A CONTACT LENS

The invention relates to a package for a contact lens for application in an eye.

Normally, a contact lens is stored with a saline solution in a container closed by a lid which is torn off when the contact lens is to be used after which the saline solution and the contact lens are poured out into the user's hand with the convex side of the contact lens facing upwards. The user can then make the wet contact lens adhere to a fingertip by a light touch and thereby use the finger for applying the contact lens.

When the user uses his hands as applicator in this way, it can hardly be avoided that the contact lens is contaminated by particulate matter and/or often bacteria-containing dirt which could irritate and damage the eye to a greater or smaller extent. To this should be added that the operation is difficult and troublesome to perform.

In order to avoid these disadvantages, applicators have been developed for holding the contact lens by means of e.g. tweezers and/or suction cups. However also in these cases, it has not been possible to ensure the contact lens sufficiently against contamination. Often, the contact lens must thus still first be poured out into one hand before the lens can be caught with the other hand by means of such an applicator which furthermore often is contaminated itself. Another problem is that the applicator is a separate aid which the user must carry around or otherwise have at hand to be able to apply a contact lens in this way.

The object of the invention is to provide a package of the kind mentioned in the opening paragraph whereby a contact lens, without the use of separate aids, can be applied more easily and in a more clean and sterile manner than known so far.

The novel and unique features according to the invention, whereby this is achieved, is the fact that the package comprises a first part arranged to, when opening the package, function as an applicator with a concave surface formed mainly complementary to the convex side of the contact lens for carrying the contact lens during application; and a second part closely joined with the first part in the unopened condition of the package and together with this first part delimiting a chamber for storing the contact lens. This structure means that the contact lens easily and quickly can be applied in the clean and sterile condition in which it is already found to be in packaged condition as the contact lens can now be taken directly from the package to the eye without at first having to come into contact with the hands or separate aids that might contaminate the contact lens.

The relatively soft and flexible contact lens is best positioned and supported in the package when its second part is formed with a mainly complementary, in relation to the concave surface of the contact lens, convex surface that, in the unopened condition of the package, is placed opposite to the convex surface at a distance which at least corresponds to the thickness of the contact lens.

The use of the package is further facilitated when its two parts are joined with a sealing that is easily broken.

In an advantageous embodiment according to the invention, the first part of the package can be formed as a fingerstall for placing on a finger and which thereby can be used for applying the contact lens without touching it which, during this, is carried by the package on its concave surface which, for the purpose, is formed on the exterior of the bottom of the fingerstall.

In a second advantageous embodiment according to the invention, the first part of the package can consist of a relatively thin sheet with projecting tongues for holding on to when the part is used as applicator, and a projection secured on the sheet with the concave surface of the package for carrying the contact lens during application formed on the free terminal surface of the projection.

In a third advantageous embodiment according to the invention, the first part of the package can be formed as an elastomeric cup with a relatively flexible side wall and a relatively rigid bottom with the concave surface of the package for carrying the contact lens during application formed on the inside. At the same time, the second part of the package can consist of a sheet closely joined with the rim of the cup in the unopened condition of the package and having a pair of opposite tongues projecting from the package. Upon use, the part of the sheet that is covering the cup opening is removed after which the cup bottom with the contact lens is evaginated through the opening with one finger while the package is held by the projecting tongues with two other fingers. The package is now transformed into an effective applicator.

In the above third embodiment according to the invention, the sheet can advantageously be made up of a relatively rigid first foil closely joined with the cup rim and having a preshaped opening delimited by this rim, and a second foil closely joined with the first foil and at least covering its opening. The cup opening is then easily and quickly cleared by merely tearing the second foil off the first.

In a fourth advantageous embodiment according to the invention, the first part of the package can consist of a tube and a displaceable piston in the tube, the concave surface of the package then being formed on the terminal surface of the piston, and the second part of the package being closely joined with the tube in the unopened condition of the package. The second part can e.g. be a sheet of e.g. metal foil which, in use, is torn off the tube after which the piston with the contact lens can be pushed a distance out of the tube and used as an applicator.

Figure 6:
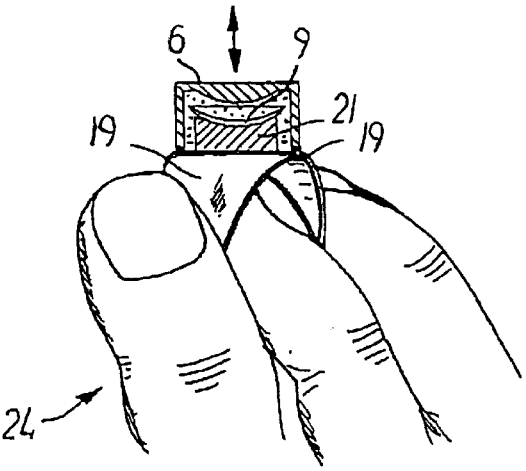
Figure 7:
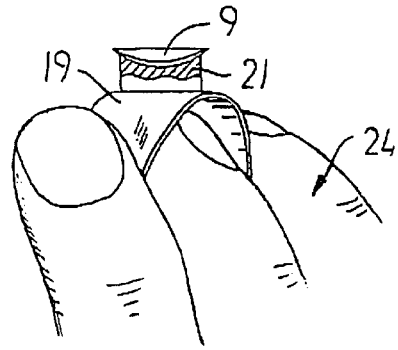
Figure 8:
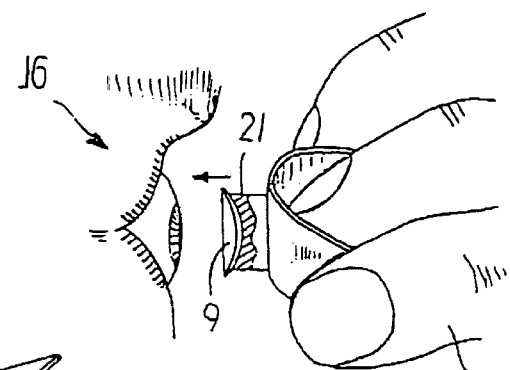
Figure 9:
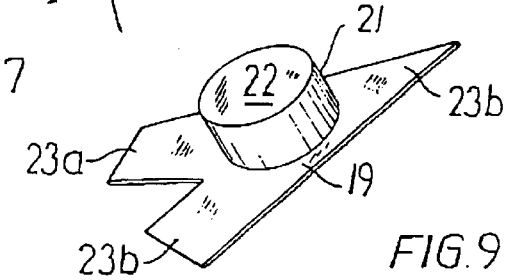
Figure 10:
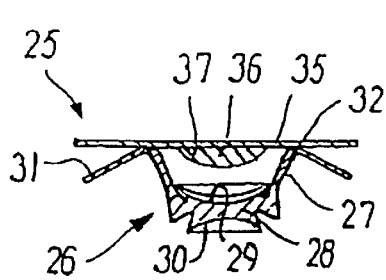
Figure 12:
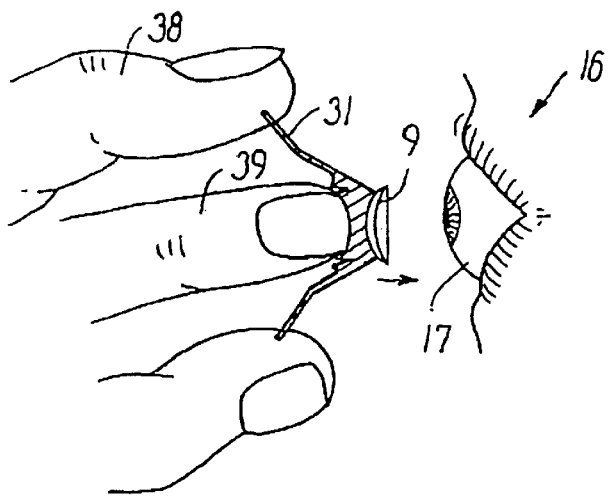
Figure 11:
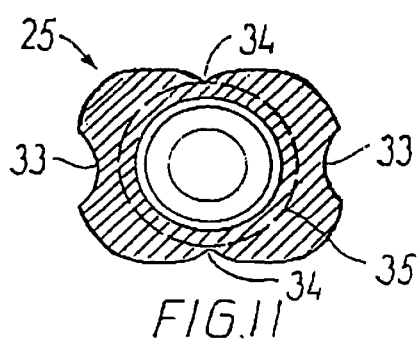
Figure 13:
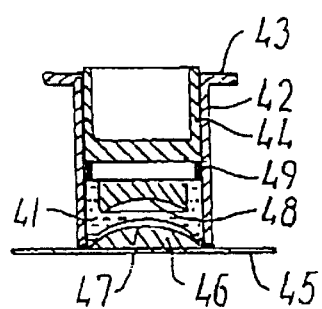
Figure 14:
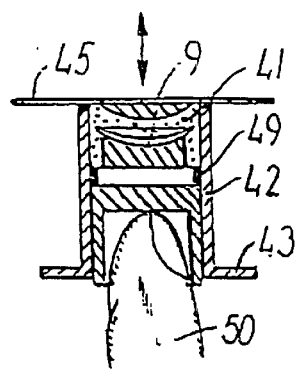
Figure 15:
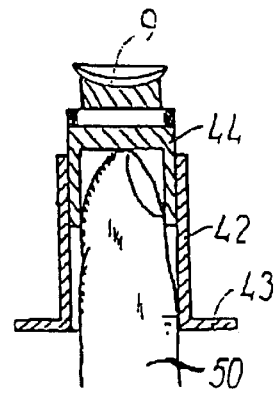
Figure 16:
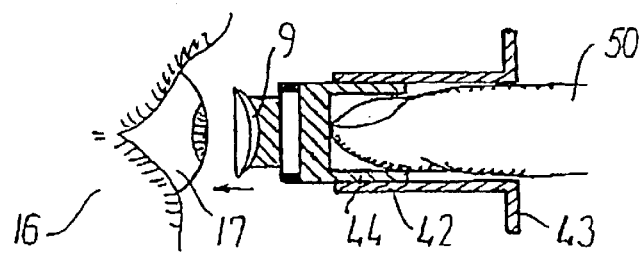

This process is especially facilitated when the piston is hollow so that the user can put a finger inside the piston in order to hold the package/applicator. The invention will be explained in greater detail below, describing only exemplary embodiments with reference to the drawing, in which FIG. 1 is an axial sectional view of a first embodiment of a package according to the invention in a position of rest, FIG. 2 is the package in FIG. 1 at a first application stage, FIG. 3 is the package in FIG. 1 at a second application stage, FIG. 4 is the package in FIG. 1 at a third application stage, FIG. 5 is an axial sectional view of a second embodiment of a package according to the invention in a position of rest, FIG. 6 is the package in FIG. 5 at a first application stage, FIG. 7 is the package in FIG. 5 at a second application stage, FIG. 8 is the package in FIG. 5 at a third application stage, FIG. 9 is a perspective view of an applicator for the package in FIGS. 5–7, FIG. 10 is an axial sectional view of a third embodiment of a package according to the invention in a position of rest, FIG. 11 is a plan view of the package in FIG. 10, FIG. 12 is a side view of the package in FIG. 11 and 12 transformed into an applicator in function, FIG. 13 is an axial sectional view of a fourth embodiment of a package according to the invention in a position of rest, FIG. 14 is the package in FIG. 13 at a first application stage, FIG. 15 is the package in FIG. 13 at a second application stage, and FIG. 16 is the package in FIG. 13 at a third application stage.

FIG. 1 shows a first embodiment 1 of a package according to the invention. The package 1 is resting upon a bed 2 and consists of a fingerstall 3 and a cup 4 closely interconnected by means of a strip-shaped sealing 5.

On the inside of the cup bottom 6, a convex surface 7 is formed which fits the concave surface 8 of a contact lens 9 lying on top of and supported by the convex surface 7 which thereby ensures the contact lens shape stability and a correct initial position during storage in the package.

The fingerstall 3 has a relatively thick bottom 10 with a concave surface 11 formed on the exterior of the bottom and fitting the convex surface 12 of the contact lens 9.

The fingerstall 3 and the cup 4 delimit a chamber 13 filled with a sterile saline solution 14.

In FIG. 2, the package 1 has now been turned upside down. The user is holding the package 1 with a finger 15 put inside the fingerstall 3, and with another finger (not shown), the user has tapped on the bottom 6 of the cup 4, as indicated with the arrow, whereby the contact lens 9 has fallen down and settled in the concave surface 11 on the exterior of the bottom 6 of the fingerstall 3.

In FIG. 3, the user has torn the strip-shaped sealing 5 off the package and removed the cup from the fingerstall. The saline solution 14 has run out of the cup while the contact lens 9 has remained in the concave surface 11 of the fingerstall.

The fingerstall 3 which still is placed on the finger 15 has, in FIG. 4, been turned to a position where the contact lens 9 is exactly opposite of the user 16's eyeball 17 only partially shown. Remaining saline solution if any has now run out of the contact lens that, due to the present moisture, has remained adhered to the concave terminal surface of the fingerstall with a relatively modest adhesive force.

From the position in FIG. 4, the contact lens 9 is then carefully brought, in the direction of the arrow, into contact with the eyeball 17. Mainly due to the capillary pressure difference between the concave and convex side of the contact lens, the contact lens will now remain adhered to the eyeball instead of the fingerstall when this is removed.

The contact lens has thus been applied to the eye without at any time coming into contact with the user's hands or separate aids which normally would be more or less contaminated. By means of the package, the contact lens can therefore be applied to the user's eye in a clean and sterile condition and without risk of the contact lens carrying foreign bodies and bacteria-containing dirt which might irritate and damage the eye.

In the second embodiment 18 of a package according to the invention shown in FIG. 5, the cup 4 is formed in the same way as the package shown in FIGS. 1–4, and equivalent components are, in the case of the cup, therefore similarly referenced.

However, the cup is now closed by a thin sheet 19 of e.g. metal foil that is closely joined with the cup rim 20 by means of e.g. an adhesive (not shown).

A projection 21 of e.g. plastic is secured on the sheet 19. In the unopened condition of the package, the projection is extending into the chamber 13 with a concave surface 22 formed on the free terminal surface of the projection and fitting the convex side 12 of the contact lens 9.

As shown best in FIG. 9, the sheet 19 has three tongues 23a,b,c that are, in the unopened condition of the package, extending past the opening of the cup 4 in such a way that they together form a convenient hold for the user's fingers 24 as shown in FIG. 6, 7, and 8.

In FIG. 6, the user has with his fingers 24 taken hold of these tongues 23a,b,c and turned the package upside down. By tapping on the cup bottom, as indicated with the arrow, the user has furthermore made the contact lens 9 fall down into the concave surface 22 on the free terminal surface of the projection 21.

In FIG. 7, the user has removed the cup 4 from the sheet 19 with the projection 21 whereby the saline solution 14 has run out while the contact lens 9 has remained in the concave surface 22 of the projection. The sheet 19 with the projection 21 now functions as an applicator which is seen in FIG. 8 at the final stage of the application process which moreover takes place in exactly the same way as described above in the case of the first embodiment.

FIG. 10 and 11 show a third embodiment 25 of a package according to the invention. In this case, the package comprises an elastomeric cup 26 with a relatively thin and flexible wall 27 and a relatively thick and rigid bottom 28.

On the inside of the cup bottom 28, a concave surface 29 is formed that fits the convex side 12 of the contact lens 9. A recess 30 is furthermore made on the exterior of the bottom.

A relatively rigid sheet 31 having an opening corresponding to the cup opening is secured on the cup rim 32 so that the two openings are flushed.

The sheet 31 has a first pair of opposite recesses 33 and a second pair of opposite recesses 34 that are angularly displaced 90° in relation to the first pair of recesses. The recesses 33 are placed at a relatively large distance from the cup rim 32 while the recesses 34 are placed with a shorter distance. As shown in FIG. 10, the parts of the sheet 31 that are in the area around the recesses 33 are bent slantingly downwards.

In FIGS. 10 and 11, the opening of the sheet 31 is tightly closed by a second plate 35 with a short projection 36 of e.g. plastic. In the unopened condition of the package, the projection is extending into the chamber 13 with a convex surface 37 formed on the free terminal surface of the projection and fitting the concave side 8 of the contact lens 9.

In FIG. 12, the user has torn the second sheet 35 off the package 25 and then, with two fingers 38, taken hold of the sheet 31 at the recesses 33 and with a pressure with a third finger 39 on the recess 30 on the bottom 28 of the cup 26, evaginated the cup out through the opening of the rigid sheet 31. The eversion is facilitated by the deep recesses 34 of the sheet 31 that are defining a bending area with a moment arm on each side for bending the sheet.

The package has now been transformed into an effective applicator for applying the contact lens 9 on the user 16's eyeball 17. Moreover, this process which is shown in FIG. 12 at its final stage takes place in the same way as described earlier in connection with the first and the second embodiment.

The sheets 31 and 35 can e.g. be of metal or plastic. It is furthermore to be noted that the package instead of two sheets 31; 35 merely can have one single sheet (not shown) with e.g. a circular weakening line to facilitate the removal of the circular area covering the cup opening.

FIG. 13 shows a fourth embodiment 40 of a package according to the invention. This structure has a chamber 40 for storing the contact lens 9 together with a saline solution 14. The chamber is delimited by a tube 42 with a reinforcing flange 43, a piston 44 displaceably placed in the tube, and a sheet 45 for tight closing of one end of the tube.

There is, on the inside of the sheet 45, secured a short projection 46 with a convex surface 47 fitting the concave side 8 of a contact lens 9 lying on top of and supported by the convex surface 47.

On the terminal surface of the piston 44 facing the short projection 46, a concave surface 48 is formed that fits the convex side 12 of the contact lens 9. The piston is furthermore hollow and sealed in relation to the tube 42 by means of a sealing ring 49.

In FIG. 14, the user has turned the package upside down and put a finger 50 into the hollow piston 44. The contact lens has fallen down into the concave surface 48 of the piston by tapping on the sheet 45 as indicated with the arrow.

In FIG. 15, the user has torn the sheet 45 off the package and with his finger 50 pushed the piston 44 a distance up through the tube 42 so that the applicator shown in FIG. 16 is formed which, in the further application process, functions in the same way as described earlier in connection with the other three embodiments.

Instead of being pushed up through the tube 42 like this, the piston 44 is pulled down through the tube in a variant not shown. In a second variant not shown, this pulling out of the piston takes place by means of a screw joint where the tube is formed as a nut and the piston as a screw.

Solid projections 21; 36; 46 are described above and shown in the drawing that are secured on sheets, 19; 35; 45 respectively, which are e.g. made of plastic or metal foil. However, the projections do not have to be solid but can within the scope of the invention just as well be recesses (not shown) formed in the respective sheets.

What is claimed is:

1. A package (1) for a contact lens (9) for application in an eye (17), the package (1) comprising a first part arranged to, when opening the package, function as an applicator with a concave surface formed mainly complementary to the convex side (8) of the contact lens (9) for carrying the contact lens during application; and a second part closely joined with the first part in the unopened condition of the package and together with this first part delimiting a chamber (13) for storing the contact lens, wherein the second part of the package (1) is formed with a mainly complementary, in relation to the concave surface of the contact lens, convex surface that, in the unopened condition of the package, is placed opposite to the convex surface at a distance which at least corresponds to the thickness of the contact lens; and wherein the first part of the package comprises a relatively thin sheet (19) with at least one free tongue (23*a,b,c*) projecting from the package; that, on this sheet, a projection (21) is placed which, in the unopened condition of the package, is extending into its chamber (13), and that the concave surface of the package is formed on the free terminal surface of the projection.

2. A package (1) according to claim 1 wherein the first part of the package consists of a tube (42) and a displaceable piston (44) tightly placed in the tube; that the concave surface of the package is formed on the terminal surface of the piston, and that the second part of the package is closely joined with the tube in its unopened condition.

3. A package (1) according to claim 2, characterised in that a hollow fitting a finger (50) and debouching in the terminal surface opposite of the concave surface of the piston is made in the piston.

4. A package (1) according to claim 1 wherein the first and the second part of the package are joined with an easily breakable sealing (5) in the unopened condition of the package.

5. A package (1) according to claim 1 wherein the first part of the package (1) is mainly formed as a fingerstall (3), and that its concave surface (11) is formed on the exterior of the bottom (10) of this fingerstall.

6. A package (1) for a contact lens (9) for application in an eye (17), the package (1) comprises a first part arranged to, when opening the package, function as an applicator with a concave surface formed mainly complementary to the convex side (8) of the contact lens (9) for carrying the contact lens during application; and a second part closely joined with the first part in the unopened condition of the package and together with this first part delimiting a chamber (13) for storing the contact lens, wherein the second part of the package (1) is formed with a mainly complementary, in relation to the concave surface of the contact lens, convex surface that, in the unopened condition of the package, is placed opposite to the convex surface at a distance which at least corresponds to the thickness of the contact lens; and wherein the first part of the package is formed as an elastomeric cup (26); that the concave surface of the part is formed on the inside of the bottom (28) of this cup, and that the second part of the package comprises a sheet (31) closely joined with the rim (32) of the first part in the unopened condition of the package (1) and having at least one free tongue projecting from the package.

7. A package (1) according to claim 6, characterised in that the cup has a relatively flexible side wall (27) and a relatively rigid bottom (28).

8. A package (1) according to claim 6 or 7, characterised in that the sheet is made up of a relatively rigid first foil closely joined with the cup rim and having a preshaped opening mainly delimited by this rim, and a second foil closely joined with the first foil and at least covering its opening.

* * * * *